United States Patent [19]

Leightley et al.

[11] Patent Number: 5,223,178
[45] Date of Patent: Jun. 29, 1993

[54] USE OF CERTAIN TRIAZOLES TO PROTECT MATERIALS FROM FUNGAL ATTACK, ARTICLES AND COMPOSITIONS

[75] Inventors: Liam E. Leightley, Gwynedd Valley; Steven H. Shaber, Horsham; Gary L. Willingham, Glenside, all of Pa.

[73] Assignee: Rohm and Haas Company, Philadelphia, Pa.

[21] Appl. No.: 625,278

[22] Filed: Dec. 10, 1990

[51] Int. Cl.$^5$ ............................. A10N 43/653
[52] U.S. Cl. ............................. 252/380; 514/383; 548/267.4; 106/18.21; 424/404
[58] Field of Search ............. 514/383; 548/267.4; 252/382, 380; 106/18.21; 424/404

[56] References Cited

U.S. PATENT DOCUMENTS

| | | | |
|---|---|---|---|
| 4,298,384 | 11/1981 | Allingham et al. | 514/520 X |
| 4,366,165 | 12/1982 | Miller et al. | 514/383 |
| 4,648,988 | 3/1987 | Van Dijck et al. | 252/602 |
| 4,677,003 | 6/1987 | Redlich et al. | 427/373 |
| 4,767,777 | 8/1988 | Bass et al. | 514/383 |
| 4,772,613 | 9/1988 | Parsons | 514/309 |
| 4,920,139 | 4/1990 | Fujimoto | 514/383 |
| 4,985,064 | 1/1991 | Redlich et al. | 71/90 |
| 5,102,898 | 4/1992 | Hsu | 514/50 |

FOREIGN PATENT DOCUMENTS

| | | |
|---|---|---|
| 0061840 | 10/1982 | European Pat. Off. . |
| 0137717 | 4/1985 | European Pat. Off. . |
| 0234683 | 9/1987 | European Pat. Off. . |
| 104367 | 6/1984 | Japan . |

*Primary Examiner*—Richard D. Lovering
*Assistant Examiner*—Valerie Fee
*Attorney, Agent, or Firm*—Michael B. Fein

[57] ABSTRACT

Specific triazoles discovered to be useful as industrial fungicides are:

1. α-n-butyl-α-phenyl-1H-1,2,4-triazole-1-propanenitrile
2. α,α-diphenyl-1H-1,2,4-triazole-1-propanenitrile
3. α-benzyl-α-phenyl-1H-1,2,4-triazole-1-propanenitrile
4. α-n-butyl-α-2-methoxyphenyl-1H-1,2,4-triazole-1-propanenitrile
5. α-n-butyl-α-4-fluorophenyl-1H-1,2,4-triazole-1-propanenitrile
6. α-phenyl-α-(2-phenylethyl)-1H-1,2,4-triazole-1-propanenitrile
7. α-(4-fluorophenyl)-α-n-propyl-1H-1,2,4-triazole-1-propanenitrile
8. α-[2-(4-chlorophenyl)ethyl]-α-phenyl-1H-1,2,4-triazole-1-propanenitrile
9. α-n-butyl-α-4-chlorophenyl-1H-1,2,4-triazole-1-propanenitrile

5 Claims, No Drawings

USE OF CERTAIN TRIAZOLES TO PROTECT MATERIALS FROM FUNGAL ATTACK, ARTICLES AND COMPOSITIONS

DESCRIPTION OF THE PRIOR ART

Van Dijck, et al., U.S. Pat. No. 4,648,988, disclose wood preserving liquids using certain azoles as active fungicidal ingredient, especially azaconazole, etaconazole, and propiconazole. These compounds have weaknesses against certain fungi.

Other triazoles have also been disclosed for wood protection. See, e.g., Japanese 59104367 of Jun. 16, 1984 to Takeda Chemical Ind. K.K.; Bass et al., U.S. Pat. No. 4,767,777; and Parsons et al, U.S. Pat. No. 4,772,613.

Other triazoles have been described as useful as agricultural fungicides but not for protection of materials such as wood, and the like, from fungal attack.

Summary of the Invention

It is an object of the present invention to provide a method of protecting materials against fungal attack.

Another object is to provide articles protected against fungal attack.

Still another object is to provide novel compositions for protection wood from fungal attack.

These objects and others as will become apparent from the following disclosure are achieved by the present invention which in one aspect comprises use of certain triazoles to protect materials against fungal attack.

In another aspect the invention comprises articles protected by the triazoles.

In yet another aspect the invention comprises fungicidal compositions comprising such triazoles.

Detailed Description of the Invention

The triazoles we have discovered to be so useful for protection against fungal attack are:
1. α-[2-(4-chlorophenyl)ethyl]-α-phenyl-1H-1,2,4-triazole-1-propanenitrile
2. α-n-butyl-α-4-chlorophenyl-1H-1,2,4-triazole-1-propanenitrile The materials which the fungicidal triazoles are capable of protecting include, for example, wood, fabric, leather, coatings, and caulks.

Articles comprising said materials and one or more of the triazoles are protected. Conventional methods of protecting materials and articles with fungicidal compounds are suitable.

Especially when wood is being protected from attack by decay causing fungi we prefer compositions comprising the triazole(s) and a quaternary ammonium compound, for example, benzylalkonium chloride.

EXAMPLE 1

This example demonstrates efficacy of several arylcyanoalkyl triazoles against a number of fungi known to cause discoloration and disfigurement of paint films commonly referred to as mildew.

The test was run as follows. Potato dextrose agar (PDA) was dissolved in water (30 g PDA/1) and autoclaved at 15 psi for 15 minutes. PDA was purchased from Difco. Triazoles were dissolved in a small quantity of methanol and added to autoclaved, molten potato dextrose agar in a dilution series to give 0.01, 0.1, 1, 10 and 100 ug ml$^{-1}$. Final methanol content of the highest dose was included. The molten agar was pipetted into Petri plates (15 ml per plate) and allowed to set. Two 5 mm mycelial plugs were removed from mother cultures of each of the fungal species tested, and were placed near the edge of the test plates. When colonies were 10–40 mm in diameter, the radial mycelial growth was measured and EC$_{75}$ values were determined on log-probit paper.

Data are shown in Table 1 for several triazoles. EC$_{75}$ values (concentration giving 75% control of hyphal growth) are reported. Structures are given in Table 3.

TABLE 1

| ORGANISM | EC 75 (ppm)$^a$ I |
| --- | --- |
| *Alternaria solani* | 5 |
| *Aspergillus flavus* | — |
| *Cladosporium resinae* | — |
| *Fusarium moniliforme* | — |
| *Fusarium oxysporum* | — |
| *Penicillium digitatum* | — |
| *Penicillium italicum* | |
| *Trichoderma viride* | | a) EC$_{75}$ = concentration giving 75% control of hyphal growth.
b) Structures are given in Table 3.

Data are shown in Table 2 for several triazoles. EC$_{50}$ values (concentration giving 50% control of hyphal growth) are reported. Structures are given in Table 3.

TABLE 2

| | EC 50 (ppm)$^a$ | |
| ORGANISM | VIII | IX |
| --- | --- | --- |
| *Aspergillus flavus* | 3.5 | 1.2 |
| *Aureobasidum pullulans* | — | 0.5 |
| *Cladisporium resinae* | 0.025 | 1.7 |

TABLE 3

Structures of Arylcyanoalkyltriazoles Tested

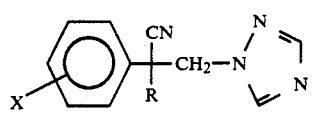

| Compound | X | R |
| --- | --- | --- |
| | H | n-C$_4$H$_9$ |
| | H | Phenyl |
| | H | CH$_2$C$_6$H$_5$ (benzyl) |
| | 2-OCH$_3$ | n-C$_4$H$_9$ |
| | 4-fluoro | n-C$_4$H$_9$ |
| | H | (CH$_2$)$_2$C$_6$H$_5$ |
| | 4-fluoro | n-C$_3$H$_7$ |
| I | H | (CH$_2$)$_2$C$_6$H$_4$(4-Cl) |
| II | 4-chloro | n-C$_4$H$_9$ |

EXAMPLE 2

This example demonstrates that the biological activity of several triazoles is not affected at pH values from 3.5 to 11.2. Data are given in Table 4.

Testing was done as follows. Chilled yeast dextrose broth inoculated with Piricularia oryzae was amended with KOH or HCl so that pH was varied as noted in Table 4. The broth was placed in microtiter plates. Acetone solutions containing 10,000 ppm of the compounds were added to a microtiter plate containing 240 microliters per well of sterile deionized water and 8 2x serial dilutions were made. Compound was added from these master plates with a 96 well metal transfer device to the inoculated broth plates. After 3 days incubation the plates were visually assessed for percent mycelial inhibition.

TABLE 4

Fungicidal Activity of Several Arylcyanoalkyltriazoles as a Function of pH

| Compound[a] | $EC_{90}$[b] (ppm) for mycelial growth pH | | | | | | | | |
|---|---|---|---|---|---|---|---|---|---|
| | 3.5 | 4.8 | 5.4 | 6.3 | 7.2 | 7.7 | 8.7 | 9.8 | 11.2 |
| I | 0.5 | 0.1 | 0.1 | 0.1 | 0.1 | 0.1 | 0.1 | 0.1 | 0.1 |
| II | 5 | 4.5 | 4.5 | 4.5 | 4.5 | 4.5 | 5 | 4.5 | 4.5 | a) Compound structures given in Table 3.
b) $EC_{90}$ = Concentration giving 90% control of hyphal growth.

EXAMPLE 3

This example demonstrates the fungicidal activity of two triazoles in paint film against two major fungal species. Testing is described below.

Testing was done in a commercial acrylic-based latex paint with conventional pigments, dispersants, and the like. The formulation utilized was a typical paint blend and is given in Table 5. Texanol (R) is trimethyl-1,3-pentanediol monoisobutyrate supplied by Eastman Chemical. "Latex" is a latex of a copolymer of butyl acrylate and methyl methacrylate.

To a sealable container was charged 100 parts of the paint formulation and the desired triazole concentration. The sample was homogenized for 15 minutes each, then blended and remixed.

Three triazoles were evaluated for their effectiveness as paint film mildewcides at 1.5 and 10 lbs/100 gallons in a laboratory popsickle stick test. Untreated controls were included in the test.

Duplicate popsickle sticks painted with the treated and untreated paint sample were inoculated with *Aureobasidium pullulans* and *Aspergillus niger*. The sticks were inoculated for 10 days at 30° C. and 95% RH and samples were rated for fungal growth.

Data is given in Table 6.

TABLE 5

| Latex Paint Formulation | | |
|---|---|---|
| Material | lb/50 gal | g/l |
| Natrosol 250 MHR hydroxyethylcellulose | 1.5 | 3.6 |
| Ethylene glycol | 12.5 | 30 |
| | Premix | |

TABLE 5-continued

| Latex Paint Formulation | | |
|---|---|---|
| Material | lb/50 gal | g/l |
| Water | 56.0 | 134.4 |
| Tamol 960 (50%) poly(methacrylic acid) | 3.6 | 8.6 |
| Potassium tripolyphosphate | 0.75 | 1.8 |
| Triton CF-10 surfactant | 1.3 | 3.1 |
| Colloid 643 thickener | 0.5 | 1.2 |
| Propylene glycol | 17.0 | 40.8 |
| Ti-Pure R-902 titanium dioxide | 112.5 | 270 |
| Minex 4 filler pigment | 79.7 | 191.3 |
| Icecap K filler pigment | 25.0 | 60 |
| Attagel 50 clay | 2.5 | 6 |
| | Let Down | |
| Latex | 153.0 | 378.1 |
| Colloid 643 | 1.5 | 3.6 |
| Texanol coalescent | 4.7 | 11.3 |
| Ammonia (28%) | 1.6 | 2.8 |
| Natrosol 250 MHR (2.5) | 53.50 | 128.4 |
| Water | 54.46 | 130.8 |
| | 581.17 | 1394.9 |

TABLE 6

Fungicidal Activity of Three Triazoles in a Paint Film Test

| Compound[a] | Treatment Level lbs/100 gal | Fungal Growth[b] | | | |
|---|---|---|---|---|---|
| | | A. niger | | A. pullulans | |
| | | replicate 1 | replicate 2 | replicate 1 | replicate 2 |
| C | | 2+ | 1+ | 3+ | 3+ |
| | | T | 0 | T | 0 |
| | | 0 | 0 | 0 | 0 |
| I | 1 | 4+ | 4+ | 2+ | 2+ |
| | 5 | 4+ | 3+ | T | T |
| | 10 | 3+ | 3+ | T | T |
| II | 1 | 3+ | 2+ | 3+ | 4+ |
| | 5 | 2+ | T | 2+ | 2+ |
| | 10 | 1+ | T | 2+ | 1+ |
| Untreated control | — | 4+ | 4+ | 4+ | 4+ | a) Compound structures given in Table 3.
b) Rating Scale
0 = No fungal growth, complete inhibition of the test organism
T = Barest trace of growth
1+ = Very light growth
2+ = Light growth
3+ = Moderate growth
4+ = Heavy growth

EXAMPLE 4

This example demonstrates the efficacy of an arylcyanoalkyl triazole against fungi known to cause decay of wood.

The test was run as follows. Potato dextrose agar (PDA) was dissolved in water (39 g/l) and autoclaved at 15 psi for 15 min. PDA was purchased from Difco. The triazole was dissolved in a small quantity of dimethylsulfoxide (DMSO) and diluted to appropriate concentrations with the same solvent. Ten microliters of the appropriate solution was added to each of five wells of a Falcon 6 well tissue culture dish. To the sixth well was added ten microliters of DMSO as a control. Five ml of molten PDA was then added to each of the wells to give 0.01, 0.1, 10 and 100 μg ml-1 of triazole. The plate was gently agitated to afford a uniform mixture. Upon cooling, the dishes were inoculated with a six mm agar plug from a freshly grown culture of the test organism. The assay plates were then incubated at room temperature and evaluated when the radial growth in the control well had reached approximately 30 mm. The radial growth for the treated wells was measured and the growth inhibition and $EC_{50}$ values were calculated using non-linear regression analysis. Data are shown in Table 7 for triazoles VIII and IX (Table). $EC_{50}$ values (concentration giving 50% control of hyphal growth) are reported.

TABLE 7

| Organism | $EC_{50}$ (ppm)[a] | |
| --- | --- | --- |
|  | Structure VIII[b] | Structure IX |
| *Gloeophyllum tradeum* | 0.158 | 0.313 |
| *Phialophora mutabilis* | 0.612 | 1.447 |
| *Poria placenta* | 0.175 | 0.228 |
| *Trametes Versicolor* | 0.061 | 0.118 | a) $EC_{50}$ = concentration giving 50% control of hyphal growth.
b) Structure is given in Table 3.

While the invention has been described with reference to specific examples and applications, other modifications and uses for the invention will be apparent to those skilled in the art without departing from the spirit and scope of the invention defined in the appended claims.

We claim:

1. A method of using a compound selected from the group consisting of α-(2-(4-chlorophenyl)ethyl)-α-phenyl-1H-1,2,4-triazole-1-propanenitrile; and α-n-butyl-α-4-chlorophenyl-1H-1,2,4-triazole-1-propanenitrile as an antifungal agent for protecting a materials from fungal attack comprising introducing said compound onto or into said material in a fungicidally effective amount.

2. Article protected against fungal attack comprising a material and a compound selected from the group consisting of α-(2-(4-chlorophenyl)ethyl)-α-phenyl-1H-1,2,4-triazole-1-propanenitrile; and α-n-butyl-α-4-chlorophenyl-1H-1,2,4-triazole-1-propanenitrile; wherein said material is selected from the group consisting of wood, fabric, leather, coatings, and caulks.

3. Composition useful for protecting materials against fungal attack comprising
   (A) compound selected from the group consisting of α-(2-(4-chlorophenyl)ethyl)-α-phenyl-1H-1,2,4-triazole-1-propanenitrile; and α-n-butyl-α-4-chlorophenyl-1H-1,2,4-triazole-1-propanenitrile and
   (B) a quaternary ammonium compound; wherein said material is selected from the group consisting of wood, fabric, leather, coatings, and caulks.

4. Composition according to claim 3 wherein said quaternary ammonium compound is benzylalkonium chloride.

5. Composition according to claim 4 wherein the ratio of (A) to (B) is about 1:1 to 1:10 by weight.

* * * * *

UNITED STATES PATENT AND TRADEMARK OFFICE
CERTIFICATE OF CORRECTION

PATENT NO.  : 5,223,178
DATED       : June 29, 1993
INVENTOR(S) : L. E. Leightley et al.

It is certified that error appears in the above-identified patent and that said Letters Patent is hereby corrected as shown below:

On the Title Page, Item [57]:

Please delete the text of the abstract and insert

--Specific triazoles discovered to be useful as industrial fungicides are:

I.  α-[2-(4-chlorophenyl)ethyl]-α-phenyl-1H-1,2,4-triazole-1-propanenitrile
II. α-n-butyl-α-4-chlorophenyl-1H-1,2,4-triazole-1-propanenitrile--

Column 1, line 40, change "1" to --I--
Column 1, line 42, change "2" to --II--

Column 1, line 54, after chloride insert --and preferably in a weight ratio of about 1:1 to 1:10. The following examples are presented to illustrate a few embodiments of the invention. All parts and percentages are by weight unless otherwise indicated.

Column 2, line 26, delete "b) Structures are given in Table 3."

Table 2, after "EC 50 (ppm)" delete footnote a and under "EC 50 (ppm)" change "VIII" to --I-- and "IX" to --II--.

Table 3, under columns "X" and "R" delete first seven lines.

UNITED STATES PATENT AND TRADEMARK OFFICE
CERTIFICATE OF CORRECTION

PATENT NO. : 5,223,178
DATED : June 29, 1993
INVENTOR(S) : L. E. Leightley et al.

It is certified that error appears in the above-identified patent and that said Letters Patent is hereby corrected as shown below:

Column 3, line 52, change "Three triazoles" to --Two triazoles--.

Table 6, in title change "Three" to --Two-- and delete "C" under the Compound column and the data pertaining to it under the remaining columns.

Table 7, change "Structure VIII" to --Structure I-- and "Structure IX" to --Structure II--.

Signed and Sealed this

Twelfth Day of July, 1994

Attest:

BRUCE LEHMAN

Attesting Officer  Commissioner of Patents and Trademarks